(12) United States Patent
Ko et al.

(10) Patent No.: US 9,132,151 B2
(45) Date of Patent: *Sep. 15, 2015

(54) METHOD FOR TREATING URINARY SYSTEM DISORDERS

(71) Applicant: Feng Chia University, Taichung (TW)

(72) Inventors: Tse-Hao Ko, Taichung (TW); Chen-Li Cheng, Taichung (TW); Ming-Chean Hung, Taichung (TW); Sheau-Yun Yuan, Taichung (TW); Shih-I Chang, Taichung (TW)

(73) Assignee: FENG CHIA UNIVERSITY, Taichung (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/337,949

(22) Filed: Jul. 22, 2014

(65) Prior Publication Data

US 2014/0335134 A1  Nov. 13, 2014

Related U.S. Application Data

(63) Continuation-in-part of application No. 12/984,683, filed on Jan. 5, 2011.

(51) Int. Cl.
| | |
|---|---|
| *A61K 9/00* | (2006.01) |
| *A61K 33/44* | (2006.01) |
| *A61K 33/38* | (2006.01) |
| *A61K 33/34* | (2006.01) |
| *A61K 9/10* | (2006.01) |
| *A61K 33/24* | (2006.01) |
| *A61K 33/30* | (2006.01) |
| *A61K 9/14* | (2006.01) |
| *A61K 45/06* | (2006.01) |

(52) U.S. Cl.
CPC ............... *A61K 33/44* (2013.01); *A61K 9/0034* (2013.01); *A61K 9/10* (2013.01); *A61K 9/14* (2013.01); *A61K 33/24* (2013.01); *A61K 33/30* (2013.01); *A61K 33/34* (2013.01); *A61K 33/38* (2013.01); *A61K 45/06* (2013.01)

(58) Field of Classification Search
CPC ..... A61K 9/0034; A61K 33/44; A61K 33/38; A61K 45/06; A61K 9/10; A61K 9/14
USPC .................................................. 424/400, 125
See application file for complete search history.

(56) References Cited

U.S. PATENT DOCUMENTS

2011/0142946 A1 * 6/2011 Tabata et al. .................. 424/489

* cited by examiner

*Primary Examiner* — Blessing M Fubara
(74) *Attorney, Agent, or Firm* — Ming Chow; Sinorica, LLC

(57) ABSTRACT

A method for treating urinary system disorders comprising: a pharmaceutical composition comprising a carbon material and a water-containing carrier, the pharmaceutical composition comprising a carbon material in an amount from 0.001 mgs to 100 mgs, both of the carbon material and the water-containing carrier constitute a pharmaceutically acceptable water-containing carrier carrying the carbon material, and the carbon material having a diameter falling within a range from 2 nm to 2 mm; Then instilled this pharmaceutical composition into the bladder for adsorb LPS of bacteria, aqueous vehicle in a volume of from 50 mL to 700 mL. After adsorb, discharging the LPS together with urine out of cystitis patients. This method is capable of reducing symptoms of cystitis by contacting the carbon material with a bladder or related tissues of the bladder in an animal body.

15 Claims, 9 Drawing Sheets

*Histological analysis of the effect of AC on LPS-induced hemorrhagic cystitis*

| Treatment groups | Edema | Leukocytes infiltration | Hemorrhage |
|---|---|---|---|
| Control | 0.50 ± 0.27 | 0.38 ± 0.18 | 0.75 ± 0.41 |
| LPS | 2.50 ± 0.27$^a$ | 2.50 ± 0.27$^a$ | 4.63 ± 0.41$^a$ |
| LPS + AC | 1.63 ± 0.26$^{a,b}$ | 1.25 ± 0.16$^{a,b}$ | 1.63 ± 0.32$^b$ |
|  | (34%) | (50%) | (64.7%) |

FIG. 6

*Histological Concentration of PCT in Rat Serum and Weight of Bladder*

| Serial Number | PCT concentration (ng/ml) | Weight of bladder (mg) |
|---|---|---|
| Normal | 0.021 | 109.8 |
| LPS | 0.036 | 177.6 |
| LPS -ACF | <0.02 | 138.1 |

FIG. 7

METHOD FOR TREATING URINARY SYSTEM DISORDERS

BACKGROUND OF THE INVENTION

1. Field of the Invention

The present invention relates to a method for treating urinary system disorders, and more particularly to use a pharmaceutical composition includes a water-containing carrier carrying a carbon material, such that both water-containing carrier and carbon material constitute a pharmaceutically acceptable water-containing carrier carrying the carbon material for treating urinary system disorders.

2. Description of the Prior Art

Urinary tract infection (UTI) is inevitable in patients received prolonged indwelling urinary catheter and the use of catheters that can result in the introduction of bacteria into the urinary bladder. In some patients with Parkinson disease, cortical strokes, brain tumors, normal pressure hydrocephalus, traumatic brain injury, Alzheimer-type dementia, and suprasacral spinal cord injury who have dysfunction of the lower urinary tract and neurologic transmission (neurologic disorder), there is a loss of coordination between the bladder and its outlet, creating an obstruction. The indications of application of urinary catheterization include bladder outlet obstruction (BOO), either functional BOO, such as spinal cord injury or organic BOO, such as prostatic hypertrophy or urethral stricture, when accurate output monitoring is required, for selected operation in the perioperative period, to assist in healing of pressure ulcer. Patients with bladder neck outflow obstruction due to benign or malignant prostatic disease require long-term use of indwelling urethral (Foley) or suprapubic catheters. The truth is the indwelling catheter impairs host defences by providing access of microorganisms to the bladder. A variety of infecting organisms involved in catheter-related UTI. The presence of bacteriuria with $10^5$ or more colony forming units per ml (CFU/ml) is the simplest way of diagnosing the cystitis. Therefore, a large quantity of bacteria in urine indicates the occurrence of cystitis or pyelonephritis. *Escherichia coli* (*E. coli*) is the most common, and other important organisms are *Enterobacter* spp., *Pseudomonas aeruginosa, Klebsiella* spp., *Serratia* spp., and *Candida* spp.

The only commonly available management techniques for neurogenic bladder dysfunction or bladder obstruction might lead to frequent UTI or sepsis, predisposition to chronic renal inflammation, chronic pyelonephritis, renal failure, and dialysis, as well as increase the risks of invasive and potentially lethal bladder cancer.

Furthermore, long-term treatment with antibiotics can result in bladder infection by resistant organisms. In one clinical study, *Escherichia coli* was shown to cause 80-85% of acute episodes of uncomplicated cystitis. *Staphylococcus saprophyticus* and other such organisms are responsible for most of the non-*E. coli* episodes.

From statistics of nosocomial infections occurred in intensive care units in Taiwan in 2007, it is found that the urinary tract infection occupies 37.5% of the total number of nosocomial infections and ranks No. 1 among all kinds of nosocomial infections in Taiwan, regardless of its occurrence in medical centers or regional hospitals. At present, the urinary system disease caused by bacterial infections in different age groups still rank the highest among urinary tract infections. In addition, an invasive treatment such as catheter insertion and cystoscopic examination is the most common treatment adopted by hospitals, and such treatment may be one of the main causes of exogenous infections, since bacteria are introduced into a bladder while there is a risk of causing an ascending bacterial infection that results in a bacterial cystitis, cause redness, swelling and vascular congestion occur at the position of the inflammation. If cystitis is treated improperly, a severe infection may occur at the bladder or incur a failure of a patient's kidney that requires dialysis later, or will even incur a risk of fatal sepsis/urosepsis.

At present, the initial therapy of patients with catheter-acquired UTI is whether oral or parenteral antibiotics. Parenteral therapy is indicated in patients with severe toxic signs, including high fever, unstable vital signs oror patients who can not tolerate oral administration. Intravesical instillation of antibiotics is an alternative approach in treatment of chronic indwelling catheter induced UTI, especially fungal urinary tract infection. The antimicrobial should be prescribed based on the urine culture results. A variety of antimicrobial agents are used for treatment of catheter-related UTI, including penicillins, cephalosporines, fluoroquinolones, aminoglycosides . . . etc. The techniques used for preventing a bacterial infection of a urinary tract include antibiotic methods, and application of coating medicine on the surface of a catheter, and using silver or silver plated catheters, etc. Recurrent UTI required multiple coursed of antibiotic therapy, thus increasing the probability of development of drug-resistant bacteria.

Although a large quantity of bacteria will be killed after taking the aforementioned medication treatments, the medication treatments also cause the production of lipopolysaccharides (LPS), and the LPS comes from the cell walls of bacteria and induces inflammatory reaction. Bladder cells to secrete cytokine including IL-1 α β, TNF-α, IL-6, IL-8 and IL-10 inflammatory factors, and such inflammatory factors play an important role for the white blood cell accumulation of a bladder and cause the characteristics of inflammation including redness, swelling, heat and pain, or even internal bleeding in a severe inflammation. The aforementioned phenomenon usually occurs in patients wearing a catheter regularly since exogenous bacterial infections causing complicated infections such as chronic cystitis are inevitable, and some patients may be attacked by severe bacterial infections or even fatal sepsis/urosepsis due to incomplete treatments. Furthermore, the treatments of cystitis or the techniques of preventing bacterial infections of urinary tracts seldom release the symptom continuously and may cause side effects in a long-term treatment and an application of the prevention techniques.

SUMMARY OF THE INVENTION

The object of the present invention is to provide a method for treating urinary system disorders the method comprise:

(a) providing a pharmaceutical composition comprising a carbon material and a water-containing carrier, said carbon material in an amount from 0.001 mgs to 100 mgs, both of said carbon material and said water-containing carrier constitute a pharmaceutically acceptable water-containing carrier carrying said carbon material, and said carbon material having a diameter falling within a range from 2 nm to 2 mm;

(b) having said pharmaceutical composition adapted for instilled into the bladder of a patient, with an aqueous vehicle in a volume of from 10 mL to 750 mL, said pharmaceutical composition adsorbing endotoxins and lipopolysaccharide (LPS) of a bacteria, said pharmaceutical composition being administered directly to the mucosa of the bladder by way of a catheter, with water-containing carrier carrying the carbon material has a content of over 0.001 mg/ml per unit dose; and (c) discharging the LPS together with urine out of said patient's body; thereby, said pharmaceutical composition reducing symptoms of cystitis.

To achieve the foregoing objective, the present invention adopts the following technical measures and uses a pharmaceutical composition for treating urinary system disorders, and the pharmaceutical composition comprises a carbon material carried by a water-containing carrier and having a carbon material in an amount from 0.001 mgs to 100 mgs, such that both of the water-containing carrier and the carbon material constitute a pharmaceutically acceptable water-containing carrier carrying the carbon material, and the water-containing carrier carries a carbon material ranging from 0.005 mg/ml to 5 mg/ml per unit dose, and the carbon material has a diameter ranging from 2 nm to 2 mm and a carbon layer stack thickness (Lc) ranging from 1 nm to 1000 mm. The carbon material further comprises a metal particle selected from the collection of silver, platinum, palladium, gold, zinc and copper particles and any combination of the above, and the metal particle has a diameter falling within a range from 2 nm to 2 mm.

The present invention further uses a pharmaceutical composition for treating urinary system disorders, and the pharmaceutical composition comprises a carbon material or a carbon material combined with metal particles and contacted with a bladder and related tissues of the bladder in an animal body, wherein a carbon material composed of active carbon can be used for adsorbing bacteria, and the low-concentration ions of a uniformly distributed fine granular metal can be used for the disinfection effect and produce an effect of quickly adsorbing bacteria and the endotoxin which is the lipopolysaccharides (LPS) produced by the cell walls of dead bacteria. Clinically, the endotoxin (LPS) will induce bladder cells to secrete cytokine including IL-1 α β, TNF-α, IL-6, IL-8 and IL-10 inflammatory factors, and such inflammatory factors play an important role of causing a white blood cell accumulation to the bladder, and characteristics of inflammation such as redness, swelling, heat and pain.

The invention is a method for treating urinary system disorders which providing a pharmaceutical composition adapted for instilled into the bladder of a patient, with an aqueous vehicle in a volume of from 50 mL to 700 mL, said pharmaceutical composition adsorbing endotoxins (lipopolysaccharide (LPS)) of a bacteria, said pharmaceutical composition being administered directly to the mucosa of the bladder by way of a catheter, with water-containing carrier carrying the carbon material has a content of over 0.001 mg/ml per unit dose; and discharging the LPS together with urine out of said patient's body; and the step of instilling is performed at least once weekly for a period of at least 6 weeks; thereby, said pharmaceutical composition reducing symptoms of cystitis.

The invention has the effects of reducing the endotoxins that causes the inflammation and reducing the symptoms of cystitis, while controlling infections effectively, preventing the recurrence of the cystitis, promoting the healing of wounds at the surface of the bladder, releasing the symptoms of cystitis, and treating and preventing cystitis, acute cystitis, chronic cystitis, hemorrhagic cystitis, bacterial cystitis, emphysematous cystitis, and interstitial cystitis, or curing patients with wounds in their bladder or urinary tract or patients with a urinary tract infection.

The invention can also achieve the effects of controlling infections, preventing the recurrence of cystitis, promoting the healing of wounds at the surface of a bladder, and releasing the symptoms of cystitis effectively.

BRIEF DESCRIPTION OF THE DRAWINGS

FIG. 6. shows a table comparing the histological analysis of the effect of AC on LPS-induced hemorrhagic cystitis;

FIG. 7. shows a table comparing the concentration of procalcitonin (PCT) in rat serum and the weight of a bladder selected from different groups of rats in accordance with a first preferred embodiment of the present invention;

DETAILED DESCRIPTION OF THE PREFERRED EMBODIMENTS

Figure 1:
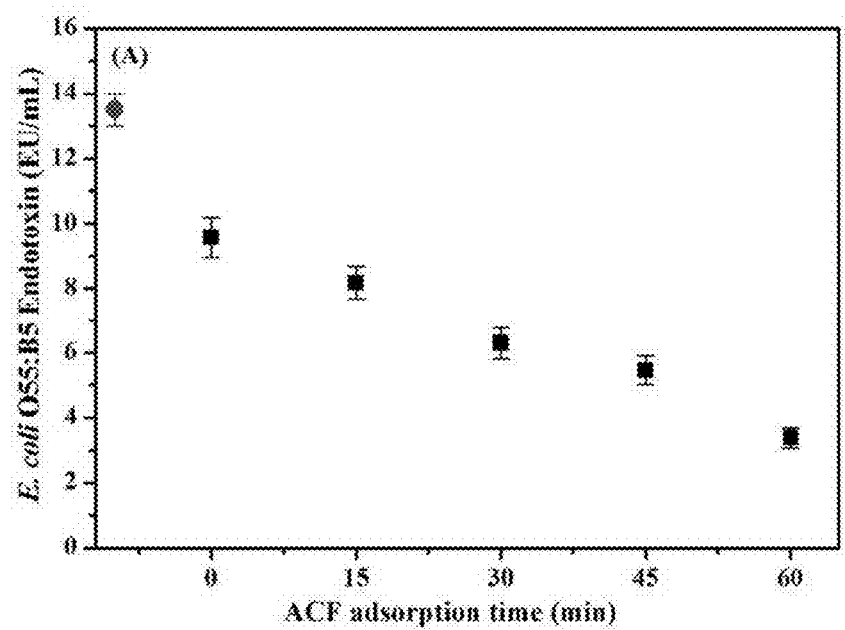
FIG. 1. shows a graph of the ACF adsorption kinetics of endotoxin (LPS; pH 7, T=37° C.). Initial concentration of LPS ("●" represents 13.5 EU/mL).

A method for use pharmaceutical composition for treating urinary system disorders in accordance with a preferred embodiment of the present invention comprises a water-containing carrier for carrying a carbon material having comprising a carbon material in an amount over 0.001 mgs, such that the water-containing carrier and the carbon material form a pharmaceutically acceptable water-containing carrier carrying the carbon material; Then instilled this aqueous pharmaceutical composition which in a volume between 50 mL to 700 mL into the bladder for adsorb LPS of bacteria. After adsorb, discharging the LPS together with urine out of cystitis patients.

Wherein the carbon material is one selected from the collection of carbon fiber, active carbon fiber, active carbon, nano-carbon tube, coke ball and carbon black, or a combination of the above, and the carbon material has a diameter falling within a range from 2 nm to 2 mm, a carbon layer stack thickness (Lc) falling within a range from 1 nm to 1000 mm, and a structure and specific surface area (BET) from 20 $m^2/g$ to 4000 $m^2/g$, wherein the carbon material of a preferred embodiment of the present invention is active carbon fiber powder or active carbon, and the carbon material in an amount from 0.01 mgs to 1 mgs, a structure and specific surface area (BET) from 700 $m^2/g$ to 1500 $m^2/g$.

In the meantime, the water-containing carrier is one selected from the collection of buffer solution, antibiotic medicament, cystitis medication, and any combination of the above, and above aqueous vehicle are normal saline and phosphate buffered saline, and the water-containing carrier carries over 0.001 mg/ml of the carbon material per unit dose, and the step of instilling is performed at least once weekly for a period of at least 6 weeks. For instilled the water-containing carrier carries 0.005 mg/ml to 1 mg/ml of the carbon material per unit dose is performed at least once weekly for a period of at least 1 week in accordance with a first preferred embodiment of the present invention preferred embodiment.

The composition and effects of the second preferred embodiment of present invention are the same as those of the first preferred embodiment, and thus will not be described here again. The carbon material of the second preferred embodiment further comprises a metal particle and the metal particle is a fine granular metal particle selected from silver, platinum, palladium, gold, zinc and copper particles or a combination of the above, and the metal particle has a diameter ranging from 2 nm to 2 mm and occupies a percentage by weight of the carbon material less than 20 wt %. In the second preferred embodiment, the fine granular metal occupies a percentage by weight of the carbon material below 5 wt %. The fine granular metal and the carbon material are combined and carried by the water-containing carrier to form the pharmaceutical composition for treating urinary system disorders.

The antibiotic medicament of the water-containing carrier is one selected from the collection of trimethoprim-sulfamethoxazole (TMP-SMX), trimethoprim (TMP), sulfame-thoxazole (SMX), fluoroquinolones, ciprofloxacin, ofloxacin, cephalexin and tetracycline or a combination of the above, and the cystitis medication of the water-containing carrier is one selected from the collection of dimethyl sulfoxide, clorpactin, heparin, hyaluronic acid (HA), adriamycin (ADM), chondroitin sulfate, sodium bicarbonate, silver nitrite, pentosan polysulfate sodium, cromolyn sodium, pencillin, nitrofurazone, gentamicin and mild silver protein, or a combination of the above.

The carbon material of the pharmaceutical composition or the carbon material combined with the metal particle can be contacted with a bladder and its related tissues in an animal body for treating and preventing urinary tract infection, catheter-associated urinary tract infection, cystitis, acute cystitis, chronic cystitis, hemorrhagic cystitis, bacterial cystitis, emphysematous cystitis, interstitial cystitis, bladder or urinary tract to cure patients with wounds and urinary tract infections, while controlling the infections effectively, preventing the recurrence of cystitis, promoting the healing of wounds at the surface of a bladder, and releasing the symptoms of cystitis. The structure, characteristics, technical measures and expected effects of the present invention will become apparent with the detailed description of preferred embodiments accompanied with related drawings as follows.

Embodiment 1

The Binding Capability of Active Carbon Fiber

Figure 2:
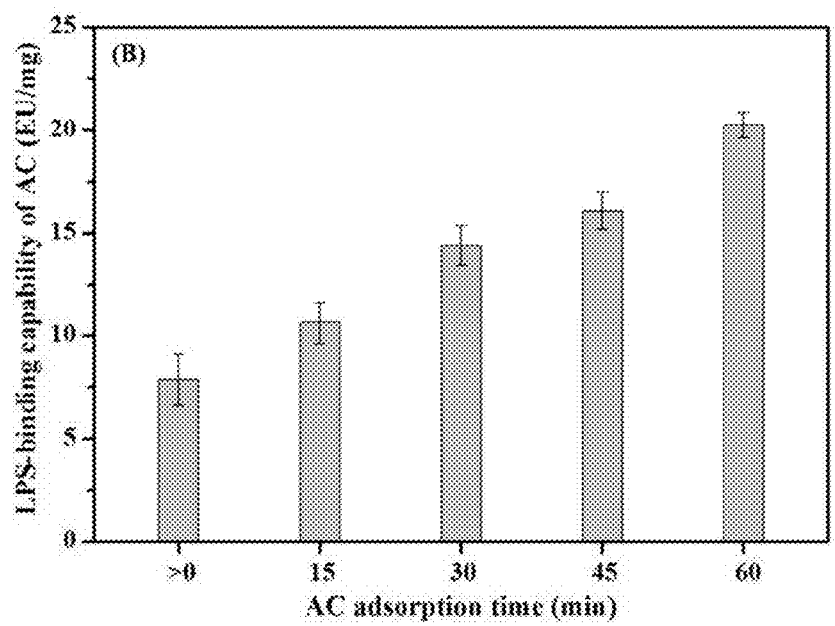
FIG. 2. shows a graph of the time course of LPS adsorption capacities by AC were 7.85±1.24, 10.63±1.02, 14.4±0.96, 16.09±0.92, and 20.24±0.62 EU/mg at 0, 15, 30, 45, and 60 min, respectively (p<0.05).

To understand and measure the LPS binding capability of composition, the first preferred embodiment was used active carbon fiber fabric (ACF) to test LPS binding capability, and the ACF has a high specific surface area (1,023 $m^2/g$) and micropore structure (approximately 55.5%). FIG. 1 shows the result for the LPS-binding capability of ACF. The result revealed that the measured LPS concentration was gradually decreased by ACF adsorption, from initial 13.5 EU/mL to 9.58 EU/mL in the early stage near "zero" time point. FIG. 2 shows the LPS-binding capability of ACF in vitro was detected using kinetic methods, expressed in linearity and in a time-dependent manner. For example, the LPS concentration decreased from 8.19 to 3.38 EU/mL at the indicated times (15, 30, 45 and 60 min) ($p<0.05$). The embodiment showed ACF had the maximum LPS binding capability at an adsorption concentration of 20.24 EU/mg at 60 min. In this preferred embodiment, ACF was applied as a carbon-based adsorption material. The result showed ACF have an excellent LPS-binding performance and confirmed that ACF can rapidly bind endotoxin (20.24 EU/mg) at 60 min. Thus, ACF is an effectively adsorbent material for binding LPS.

Embodiment 2

Administration Active Carbon Fiber Suspension Composition in SD-Rat Model and Evaluat Edema and Histopathological of Bladder Preparation of Active Carbon Fiber Suspension With the all preferred embodiment, the carbon material of the pharmaceutical composition is an active carbon fiber, the active carbon fiber produced and sold by TAIWAN CARBON TECHNOLOGY CO., LTD, and grounded into particles of with a diameter from 50 μm to 100 μm, and the structure and specific surface area (BET) of the carbon material is 700 $m^2/g$~1500 $m^2/g$, and the water-containing carrier of this preferred embodiment of the present invention is a buffer solution, and the buffer solution is preferably a sterile water, wherein the carbon material is added into the buffer solution and mixed thoroughly to form the water-containing carrier carrying the carbon material, and the water-containing carrier carries 0.2 mg/ml of the carbon material per unit dose.

Preparation of In-Vivo Experimental

In the first step, female rats were anesthetized with urethane (1.2 g/kg subcutaneously) and then catheterized through the urethra by using a lubricated PE-50 catheter in order to evacuate the residual urine in bladders by gentle aspiration (all groups).

The second step was induction of cystitis. The rats were administered 0.5 mL protamine sulfate (10 mg/mL) instilled into the bladder and retained for 45 min; the bladders were then emptied and washed with saline. After 2 h, the bladders were emptied, and the rats were then administered 0.5 mL (5 mg/kg) LPS once for 1 h (LPS group and AC group).

After 1 h, the bladders were emptied, and the rats were subjected to the third treatment with 0.5 mL (0.4 mg/kg) AC once for 1 h (AC group). After the end of the last treatment, the rats were injected with gentamicin (6 mg) to decrease the chances of any subsequent infection. The catheters were then gently removed, and the animals were allowed to recover. All rats were euthanized 24 h after the last instillation. The bladders were removed and immersed in buffered formalin for morphological analysis.

Histological Evaluation of Cystitis

Twenty-four hours after cystitis was induced, the bladders were dissected. For each rat, the dissected bladder was fixed in 10% formalin and routinely processed and embedded in paraffin wax. Two-micrometer sections were stained with hematoxylin and eosin (H&E). The urinary bladders were evaluated included mucosal inflammatory cell infiltration and the presence of interstitial edema and hemorrhage. Briefly, the edema in each quadrant was evaluated using a scale as follows: 0=no edema; 1=mild edema, not expanding the width of the submucosa; 2=moderate edema, expanding the mucosal region less than double the normal size; and 3=severe edema, doubling the area of the mucosal region or greater. Leukocyte infiltration in each section was evaluated using a scale as follows: 0=no leukocyte infiltration per $mm^2$; 1=mild infiltration or less than 30 leukocytes found per $mm^2$; 2=moderate infiltration, i.e., between 30 and 60 leukocytes per $mm^2$; and 3=severe infiltration, or greater than 60 leukocytes present per $mm^2$. The areas of hemorrhage for each cross-section were divided by 10. If a cross-section had an area of hemorrhage greater than 9, it was considered confluent hemorrhage and scored as 10. {FIG. 5 and FIG. 6 shows the control group was saline alone; LPS, (5 mg/kg) lipopolysaccharide; LPS+AC, after treatment with LPS for 1 h, AC was instilled at 0.4 mg/kg. (%) indicated [LPS−(LPS+AC)]/LPS×100%. [a]$p<0.05$ LPS or LPS+AC compared with the control group. [b]$p<0.05$ LPS+AC group compared with LPS alone. Values are means±SEM. n=10 rats in each group}.

Measurement of Vesical Edema

Vesical vascular edema was quantified as bladder wet weight (BWW), and plasma protein extravasation was measured using the Evans blue dye leakage technique. Anesthesia was induced by intraperitoneal administration of urethane (1.2 g/kg). The external jugular vein was cannulated for injecting Evans blue dye (50 mg/kg) at a dose volume of 25 mg/mL in PBS. The dye was administered 30 min before the animal was exsanguinated by infusion of 50 mL of 0.9% w/v saline into the left cardiac ventricle at 37° C. The urinary bladder was then removed and blotted dry before weighing, and the content of dye was determined by spectrophotometry (at 630 nm) after extraction in 1 mL of DMSO at 56° C. for 24 h. Plasma protein extravasation was expressed as the content of Evans blue dye in micrograms per gram of tissue. {FIG. 3 and FIG. 4: *$p<0.05$ compared to the control group. #$p<0.05$ compared to the LPS+AC group. **$p<0.01$ compared to the control or LPS+AC group. n=10 rats in each group. (%) indicated [LPS−(LPS+AC)]/LPS×100%}.

Statistical Analysis

The results are reported as mean±S.E.M. for all data on the basis of at least 5 determinations. Values with $p<0.05$ were considered as statistically significant. For histopathological data, statistical evaluation was performed using Kruskal-Wallis nonparametric analysis of variance followed by Mann-Whitney U test.

Administration Result:

Vesical Vascular Edema

Figure 3:
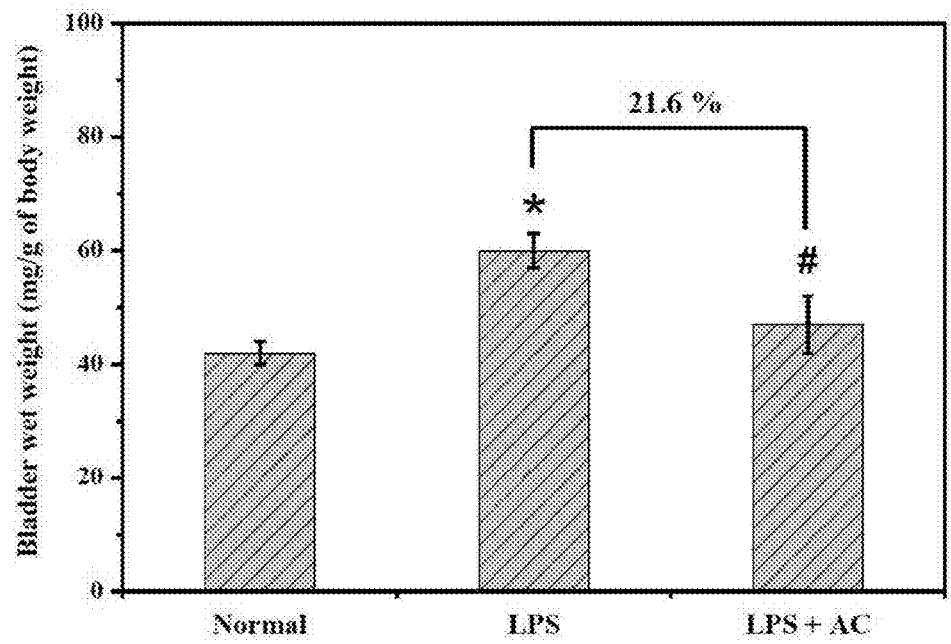
FIG. 3. shows a graph of the effect of AC against LPS-induced wet weight increase in bladders. The inflammation induced (LPS) an increase in BWW compared to that of the control, and AC inhibited this effect. *Significant (p<0.05) reduction in BWWs in the LPS+AC group vs. the LPS treatment group.
Figure 4:
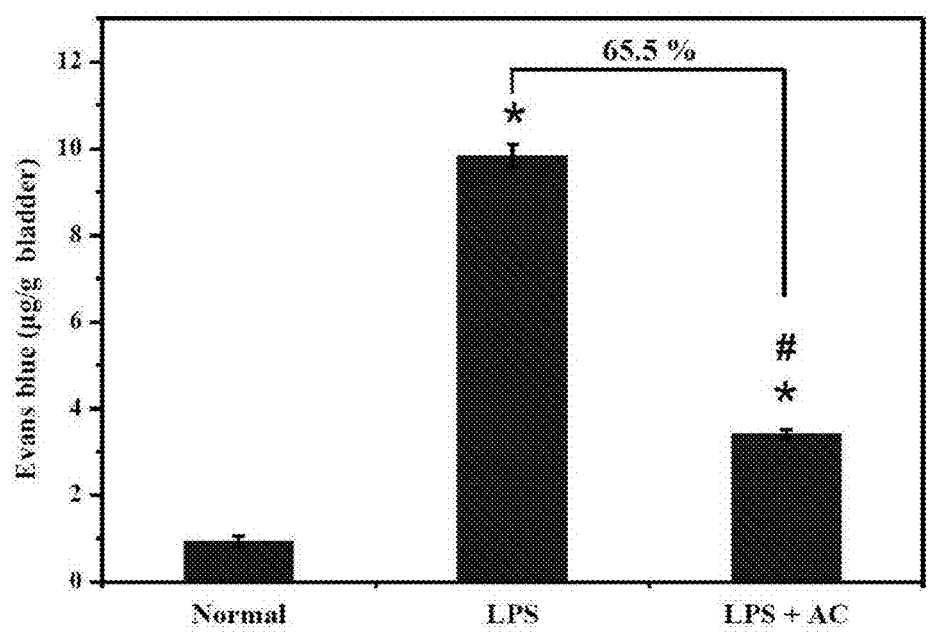
FIG. 4. shows a graph of the effect of AC against Evans blue extravasation increase in bladders. Inflammation induced (LPS) an increase in Evans blue extravasation compared to that in the control.
Figure 5A:
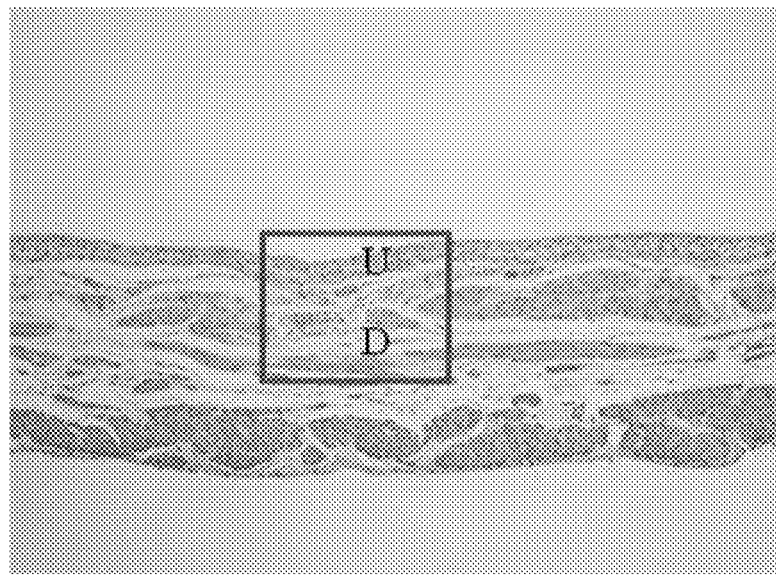
FIG. 5(a). Histopathological findings of LPS-induced cystitis in rats: normal structure of the urinary bladder in a normal female rat (100×). (U=urothelium, D=detrusor muscle)
Figure 5B:
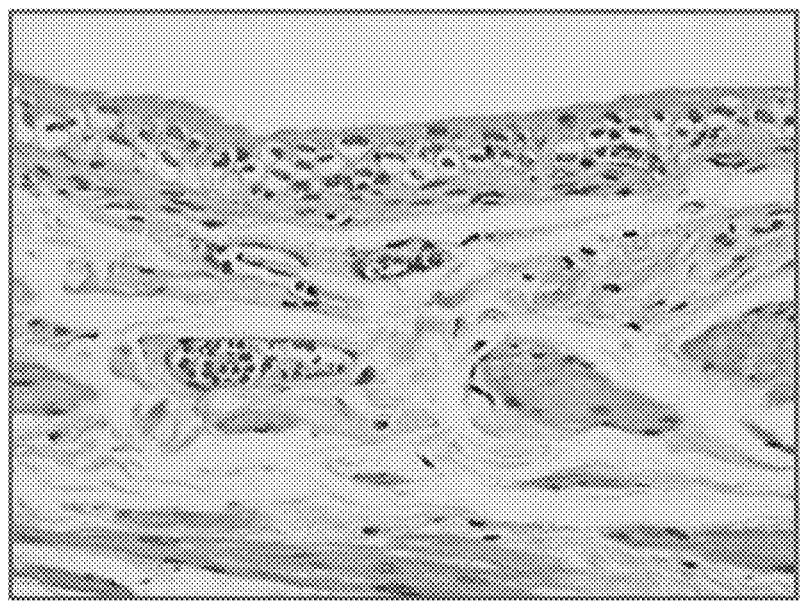
FIG. 5(b). Histopathological findings of LPS-induced cystitis in rats: normal structure of the urinary bladder in a normal female rat (400×).
Figure 5C:
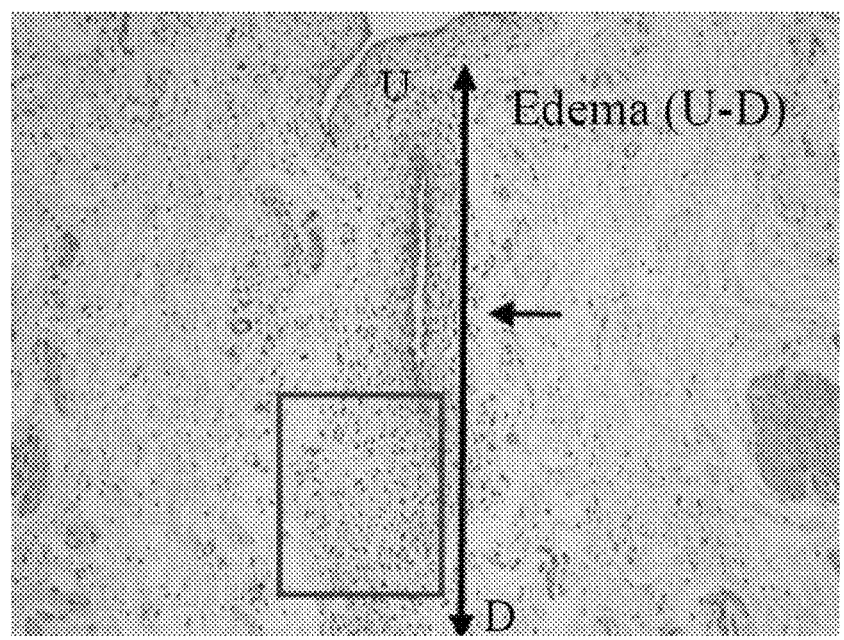
FIG. 5(c). Histopathological findings of LPS-induced cystitis in rats: LPS (5 mg/kg) induced urothelial cell injury of the urinary bladder in a female rat (100×). Note: extensive leukocyte infiltration (arrowheads) in the bladder submucosa; edema shows greater urothelium separation from the detrusor muscle within the bladder submucosa of rats of the control group compared to that in the AC group. (U=urothelium, D=detrusor muscle)
Figure 5D:
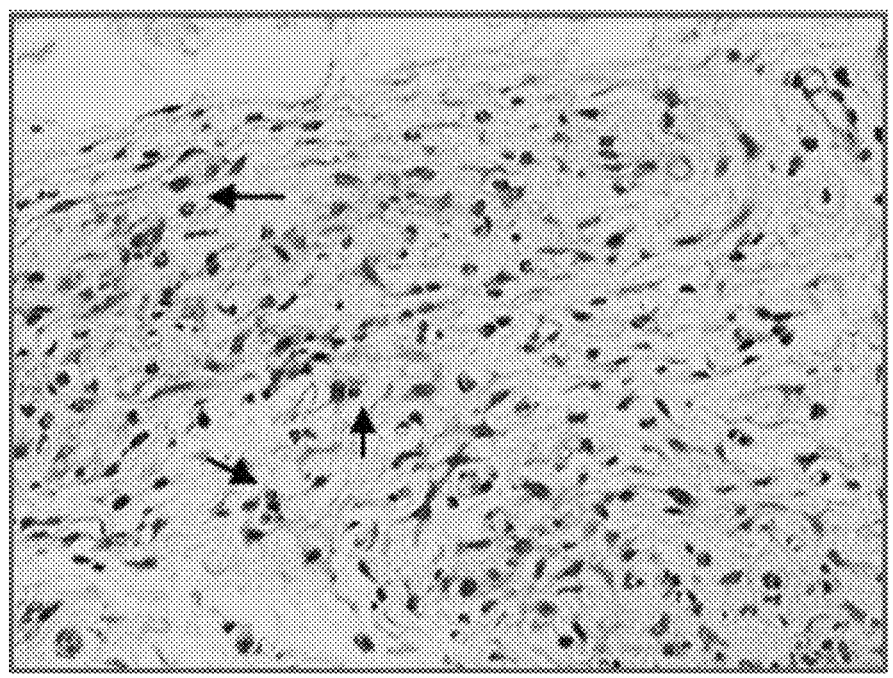
FIG. 5(d). Histopathological findings of LPS-induced cystitis in rats: LPS (5 mg/kg) induced urothelial cell injury of the urinary bladder in a female rat (400×). Note: extensive leukocyte infiltration (arrowheads) in the bladder submucosa.
Figure 5E:
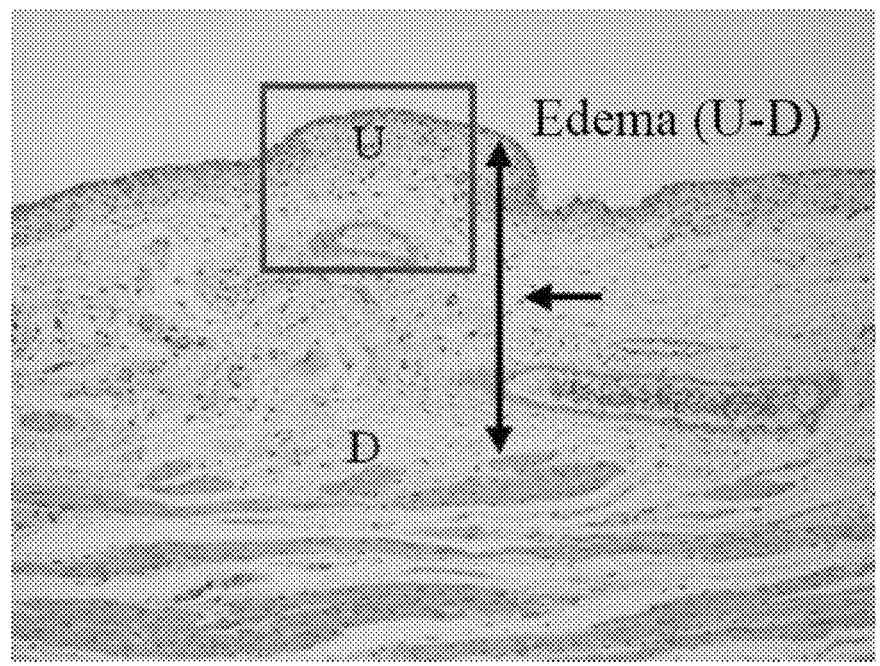
FIG. 5(e). Histopathological findings of LPS-induced cystitis in rats: LPS (5 mg/kg) induced urothelial cell injury of the urinary bladder in a female rat, and then treated by administered AC (0.2 mg/mL) (100×). (U=urothelium, D=detrusor muscle)
Figure 5F:
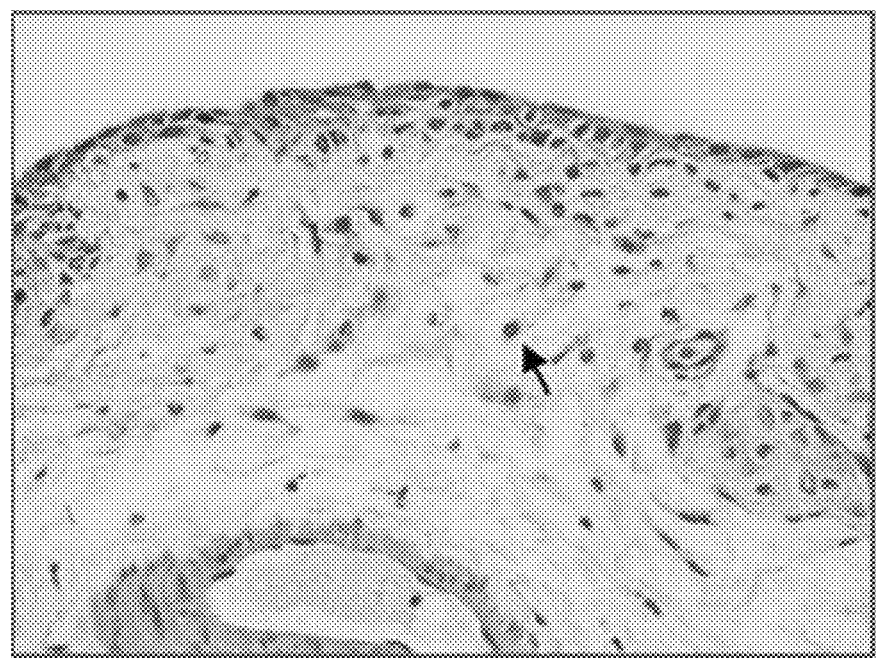
FIG. 5(f). Histopathological findings of LPS-induced cystitis in rats: LPS (5 mg/kg) induced urothelial cell injury of the urinary bladder in a female rat, and then treated by administered AC (0.2 mg/mL) (400×).

With three groups, control group was saline alone; LPS group, (5 mg/kg); LPS+AC group, after treatment with LPS for an hour, AC was instilled at 0.2 mg/mL. In the control (saline) group, the BWWs of the control, LPS, and AC groups were 42, 60, and 47 mg/100 g body weight, respectively. The BWWs of the LPS group were significantly higher than those of the control group. Similarly, the LPS group had a significantly higher BWWs than those of the AC groups by 21.6% ($p<0.05$), as shown in FIG. 3.

Furthermore, LPS induced extravasation of Evans blue in the bladder (9.83±0.27 g/g bladder tissue, 90.5% increase, $p<0.05$) compared with that in the control group (0.93±0.12 g/g bladder tissue). AC treatment significantly reduced the LPS-induced extravasation of Evans blue by 65.5% was shown in FIG. 4.

The results showed that AC (0.2 mg/mL) treatment significantly decreased BWW and Evans blue extravasation in the bladder (the parameter used to detect vascular permeability) induced by LPS (5 mg/kg).

Histopathological Evaluation

Histologic analysis showed that LPS induced not only macroscopic urinary bladder weight increase (edema) and a marked increase in vascular congestion and hemorrhage but also microscopic alterations such as mucosal sloughing, edematous submucosa, neutrophil infiltration, lymphocyte infiltration, RBC extravasation, and vessel thrombosis (arterial or venous) in the rats (FIG. 5(a)-FIG. 5(f)). The histological scores were edema (2.5), leukocytes infiltration (2.5), and hemorrhage (4.63). In contrast, 0.2 mg/mL AC significantly decreased the degree of edema (1.63), inflammatory cell infiltration (1.25), and hemorrhage (1.63) in the animals ($p<0.05$). The percentage of each investigated sample was significantly decreased by 34%, 50%, and 64.7%, respectively (FIG. 5 and FIG. 6). Thus, the in vivo study indicated that AC can decrease the BWW, Evan's blue extravasation (vesicular permeability), submucosa edema, neutrophil infiltration, and hemorrhage, which were caused by LPS. AC might therefore have a potential as an alternative therapeutic treatment for clinical bladder disease.

Embodiment 3

Administration Active Carbon Fiber Suspension Composition as Described in Embodiment 1 to SD-Rat Model and Measures the Content of the Procalcitonin (PCT)

With reference to FIGS. 7 to 10, this preferred embodiment is substantially the same as the first preferred embodiment of the present invention, and thus will not be described here again, but this preferred embodiment measures the content of the procalcitonin (PCT) in the rat serum, and the concentration of the procalcitonin in the rat serum is an important index for determining a severe bacterial infection and a generalized inflammation, so that if the concentration of the procalcitonin rises, it shows that the cystitis is a bacterial infection, a sepsis/urosepsis shock or other severe generalized bacterial infections.

In FIG. 7 show the M1-1 (Normal) group is a control of normal rats, whose concentration of procalcitonin is 0.021 ng/ml, and the M1-2 (LPS) group of inflamed rats are induced by the inflammation inducer, and whose concentration of procalcitonin is increased to 0.036 ng/ml, and the M1-3 (LPS-ACF) group of inflamed rats are induced by the inflammation inducer and injected with the pharmaceutical composition of the invention has a concentration of procalcitonin of 0.02 ng/ml. The comparison shows that the concentrations of procalcitonin in the rats of the M1-3 (LPS-ACF) group and the M1-1 (Normal) group are substantially the same. In the meantime, the weight of bladder of the rat of the M1-2 (LPS) group is 177.6 mg, and the weight of the bladder of the rat of M1-3 (LPS-ACF) after the treatment drops to 138.1 mg. Obviously, the pharmaceutical composition containing the water-containing carrier together with the carbon material has a treatment effect to cystitis.

Figure 8A:
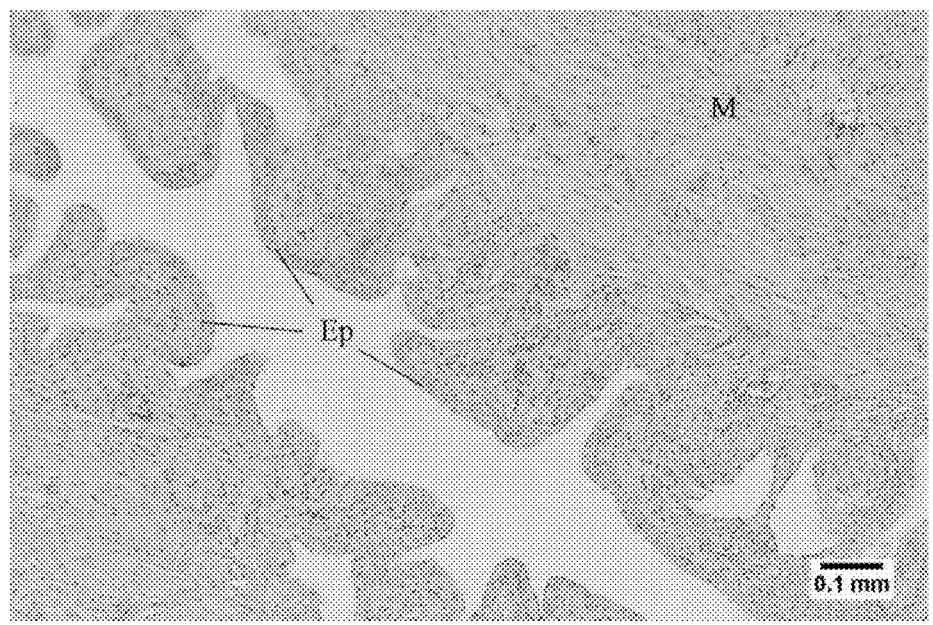
FIG. 8(a). shows a H & E stained slice of a bladder selected from the group of M2-1 (Normal) rats in accordance with a first preferred embodiment of the present invention.
Figure 8B:
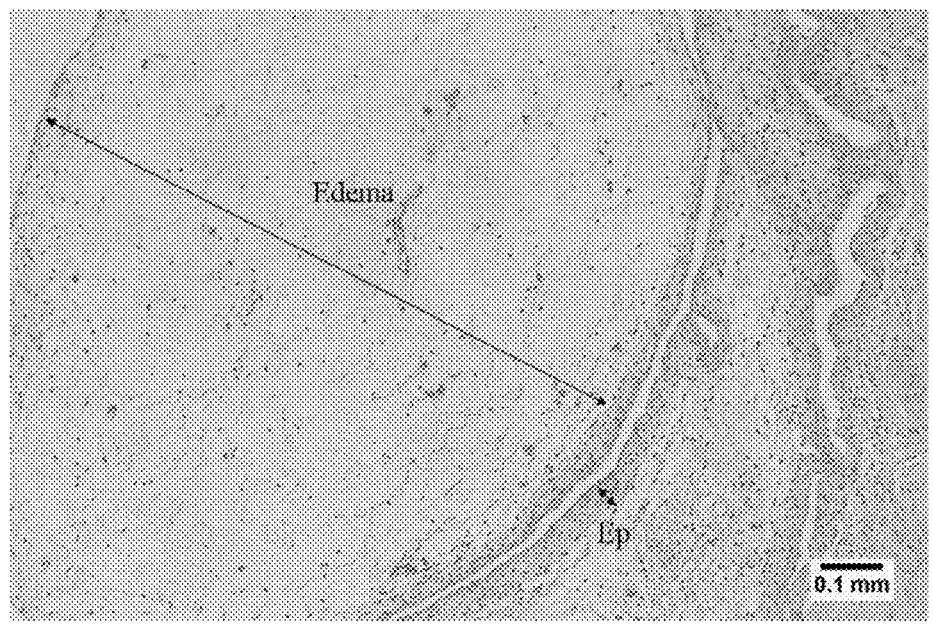
FIG. 8(b). shows a H & E stained slice of an inflamed bladders selected from the M2-2 (LPS) group and induced by a inflammation inducer in accordance with a first preferred embodiment of the present invention, and the left side of the figure indicates the occurrence of an extremely severe edema.
Figure 8C:
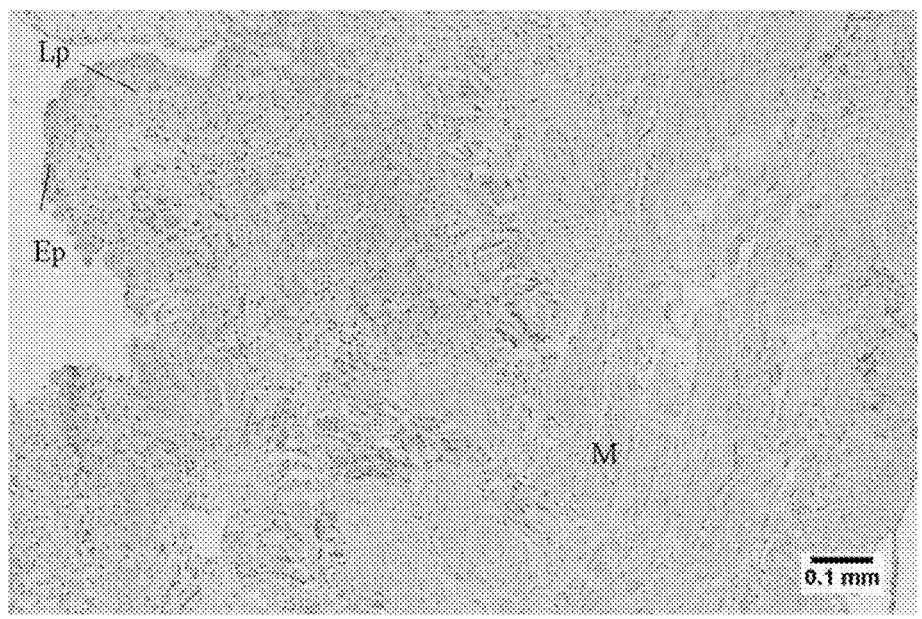
FIG. 8(c). shows a H & E stained slice of an inflamed bladder selected from the M2-3 (LPS-ACF) group and induced by a inflammation inducer after a treatment of injecting a pharmaceutical composition of a carbon material carried by a water-containing carrier in accordance with a first preferred embodiment of the present invention.

In FIG. 8(a)-FIG. 8(f) for H & E stained pathological tissue slices of bladders of rats from different groups respectively, the slide of the bladder tissue of the rat of the M1-1 (Normal) group as shown in FIG. 8(a). The FIG. 8(b) show a smooth bladder mucosa, and the slide of the bladder tissue of the rat of the M1-2 (LPS) group. The FIG. 8(c) show a severe edema on the left side of the figure, and the slide of the bladder tissue of the rat of the M1-3 (LPS-ACF) group. The result of LPS-ACF group shows a smooth surface of the bladder mucosa and no severe inflammation symptom including white blood cell accumulation, edema and internal bleeding. It shows that the pharmaceutical composition containing the water-containing carrier together with the carbon material has produced a treatment effect to the inflamed bladder.

Embodiment 4

Administration Active Carbon Fiber Support Silver Suspension in SD-Rat Model Preparation of Active Carbon Fiber Support Silver Particles The raw material of active carbon fiber (ACF) is produced and sold by CHALLENGE CARBON TECHNOLOGY CO., LTD, and the BET surface area is 1050 $m^2/g$. The activated carbon fiber cloth impregnated with an aqueous solution of 0.1 M silver nitrate (pH=3.8) for 5 hours. Thereafter, dehydration, drying and removal of the aqueous phase at 120° C. After impregnation, active carbon fiber cloth was pyrolysis under nitrogen (In 4° C./min heating rate from room temperature to 400° C., then keep for 90 minute, and then in 10° C./min cooling rate to room temperature). After pyrolysis, wash ACF cloth with water for 2 hours, and then dried at 120° C. for 2 hours to obtain the finished product.

The product of active carbon fiber cloth support silver particles (ACF/Ag) showed that the silver content of the resulting product is 0.03% by weight of the total weight, the diameter size of the silver particles on the carbon fiber is 10 to 50 nm. The true density of ACF/Ag is 2.13 $g/cm^3$, and measures the carbon content of 85.6 wt %, oxygen content of 10.5 wt %, BET specific surface area of 1,220 $m^2/g$. The silver recipitation of ACF/Ag in water of about 15.75 ppm Preparation of in-vivo Experimental In the first step, female rats were anesthetized with urethane (1.2 g/kg subcutaneously) and then catheterized through the urethra by using a lubricated PE-50 catheter in order to evacuate the residual urine in bladders by gentle aspiration (all groups).

The second step was induction of cystitis. The rats were administered 0.5 mL protamine sulfate (10 mg/mL) instilled into the bladder and retained for 45 min; the bladders were then emptied and washed with saline. After 2 h, the bladders were emptied, and the rats were then administered 0.5 mL (5 mg/kg) LPS once for 1 h (LPS group and ACF/Ag group).

After 1 h, the bladders were emptied, and the rats were subjected to the third treatment with 0.5 mL (0.2 mg/mL) ACF/Ag once for 1 h (ACF/Ag group). After the end of the last treatment, the rats were injected with gentamicin (6 mg) to decrease the chances of any subsequent infection. The catheters were then gently removed, and the animals were allowed to recover. All rats were euthanized 24 h after the last instillation. The bladders were removed and immersed in buffered formalin for morphological analysis.

Administration Result:

Antimicrobial Activity

The antimicrobial activity of ACF/AG demonstrated that bacterial colony growth decreased by 99.9% as evaluated by the quantitative AATCC 100 test against both representative gram-positive (*Staphylococcus aureus*) and gram-negative (*Escherichia coli, Pseudomonas aeruginosa* and *Klebsiella pneumoniae*) bacteria. Comparable evaluation of ACF demonstrated no reduction (0%) in growth of *Klebsiella pneumoniae*, 70.87% reduction in growth of *Escherichia coli*, 99.02% reduction in growth of *Pseudomonas aeruginosa* and 99.3% reduction in growth of *Staphylococcus aureus*.

Histopathological Evaluation

Figure 8D:
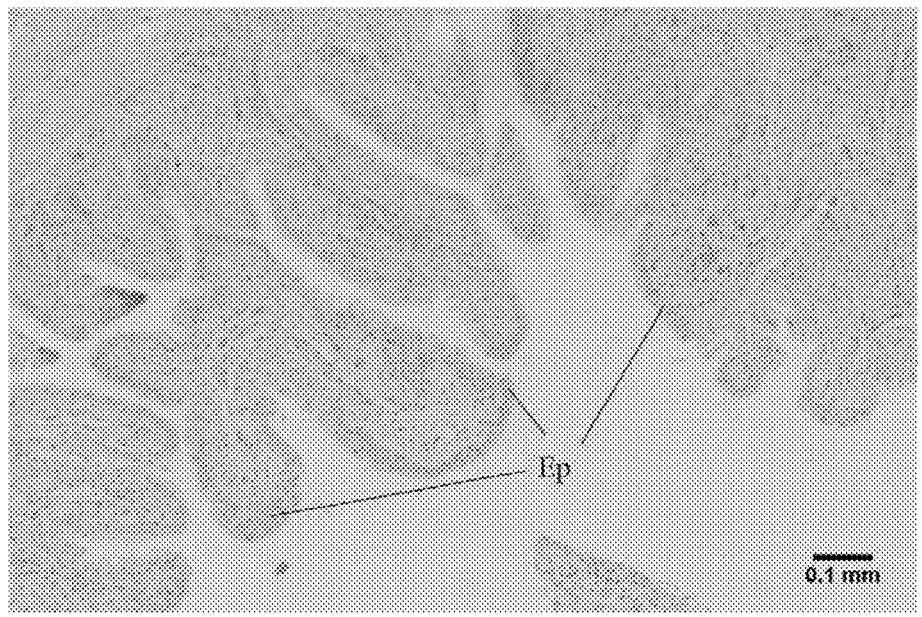
FIG. 8(d). shows a H & E stained slice of a bladder selected from the M3-1 (Normal) group in accordance with a second preferred embodiment of the present invention.
Figure 8E:
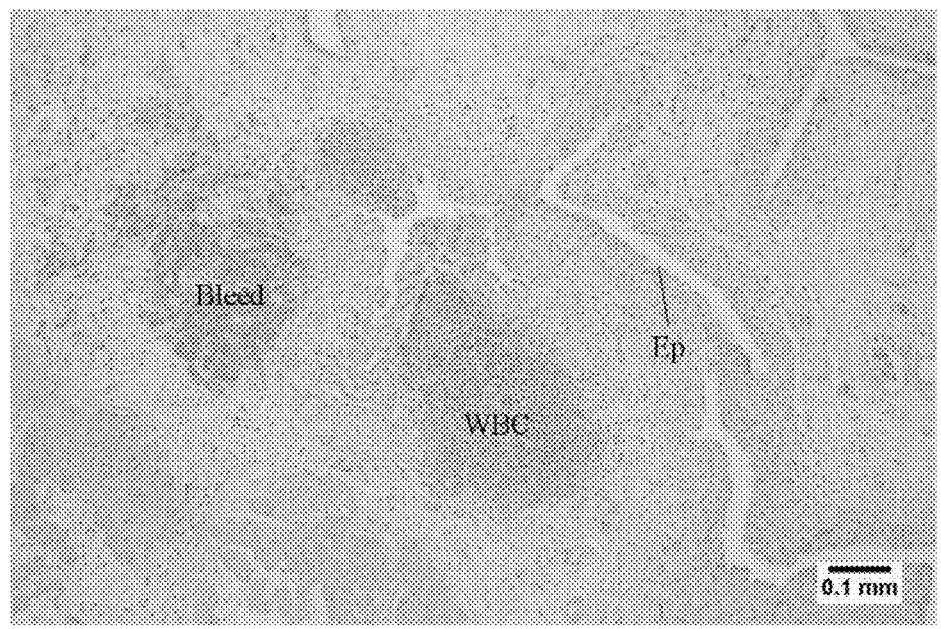
FIG. 8(e). shows a H & E stained slice of an inflamed bladder selected from the M3-2 (LPS) group and induced by a inflammation inducer in accordance with a second preferred embodiment of the present invention, and the left side of the figure indicates the occurrence of a white blood cell accumulation and an internal bleeding.
Figure 8F:
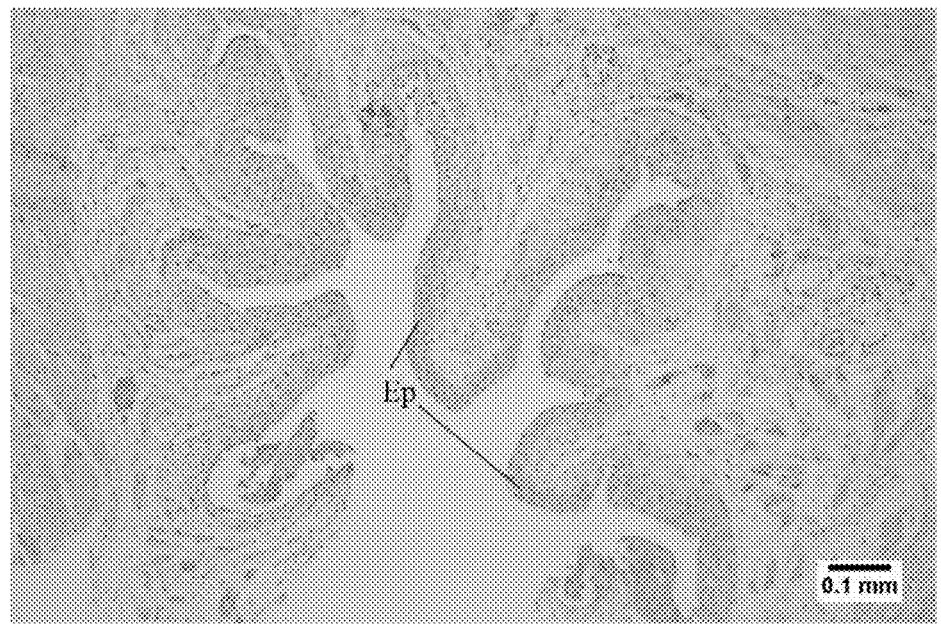
FIG. 8(f). shows a H & E stained slice of an inflamed bladder selected from the M4-3 (LPS-ACF) group and induced by a inflammation inducer after a treatment of injecting a pharmaceutical composition of a carbon material containing silver particles carried by a water-containing carrier in accordance with a second preferred embodiment of the present invention.

With reference to FIG. 8(d) to FIG. 8(f) for H & E stained pathological tissue slices of rat bladders of different groups respectively, this preferred embodiment is substantially the same as the first preferred embodiment of the present invention, and thus will not be described here again, but the pharmaceutical composition injected to the rat of the LPS-ACF/Ag for treating cystitis in accordance with a second preferred embodiment of the present invention includes a metal particle combined with the carbon material and carried by the water-containing carrier to produce the pharmaceutical composition, and the metal particle of the second preferred embodiment is a nanoscale sliver particle. With reference to FIG. 8(d) for a H & E stained slice of a normal rat bladder of the Normal group, no inflammation, edema or internal bleeding is found. The FIG. 8(e) is for an inflamed bladder of the rat of the LPS group and induced by the inflammation inducer. The result show no characteristics of severe inflammation including white blood cell accumulation, edema and internal bleeding are found. In FIG. 8(f), the rat of the LPS-ACF/Ag induced by the inflammation inducer and injected with the carbon material containing silver particles for the treatment, no characteristics of severe inflammation including white blood cell accumulation, edema and internal bleeding are found. Therefore the pharmaceutical composition produced by combining the carbon material and the silver particles has the disinfection effect and reducing the symptoms of cystitis.

In summation of the description above, the present invention has the following advantages and effects:

1. The physical method for use pharmaceutical composition for treating urinary system disorders in accordance with the present invention includes a carbon material carried by a water-containing carrier, such that both of the carbon material and the water-containing carrier constitute a pharmaceutically acceptable water-containing carrier carrying the carbon material, which is cheaper and acceptable to a bladder mucosa to release the symptoms of cystitis and provide a long-time treatment effect.

2. The method for use pharmaceutical composition for treating urinary system disorders in accordance with includes a carbon material carried by a water-containing carrier, such that both of the carbon material and the water-containing carrier constitute a pharmaceutically acceptable water-containing carrier carrying the carbon material for repairing the bladder mucosa to achieve the effect of further treatments.

3. The method for use pharmaceutical composition for treating urinary system disorders in accordance with includes a carbon material having a metal particle selected from the collection of silver, platinum, palladium, gold, zinc, copper, and a combination of the above, and the metal particle has a diameter from 2 nm to 2 mm, such that the carbon material combined with nanoscale metal particles can enhance the disinfection effect and reduce the symptoms of cystitis.

4. The method for use pharmaceutical composition for treating urinary system disorders in accordance with includes a carbon material having a higher structure and specific surface area (BET), a remarkable LPS adsorption capability (20.24 EU per mg AC for 60 min), a good biological compatibility, reduce the side effects of antibiotics, retard the inflammation action of cystitis, and achieve the expected effects.

In summation of the description above, the present invention improves over the prior art and complies with patent application requirements, and thus is filed for patent application.

While the invention has been described by device of specific embodiments, numerous modifications and variations could be made thereto by those generally skilled in the art without departing from the scope and spirit of the invention set forth in the claims.

What is claimed is:

1. A method for treating urinary system disorders, the method comprising:
   (a) providing a pharmaceutical composition, which comprises a carbon material carried by a water-containing carrier and having a carbon content over 60 percentage by weight (wt %), such that both of the carbon material and the water-containing carrier constitute a pharmaceutically acceptable water-containing carrier carrying the carbon material, and the carbon material having a diameter falling within a range from 10 nm to 2 mm; thereby, the pharmaceutical composition of the water-containing carrier carrying the carbon material is capable of reducing symptoms of cystitis by contacting the carbon material with a bladder or related tissues of the bladder in an animal body;
   (b) administering said pharmaceutical composition directly to a mucosa of a bladder of a patient by way of a catheter, with a water-containing carrier carrying said carbon material that has a content of over 0.001 mg/ml per unit dose, wherein said pharmaceutical composition is adapted to be instilled into the bladder with an aqueous vehicle in a volume of from 10 mL to 750 mL, and wherein said pharmaceutical composition adsorbs endotoxins and lipopolysaccharide (LPS) of a bacteria; and
   (c) discharging the LPS together with urine out of said patient's body; thereby, said pharmaceutical composition reducing symptoms of cystitis.

2. The method for treating urinary system disorders as recited in claim 1, wherein said carbon material carried in the water-containing carrier has a concentration per unit dose ranging from 0.005 mg/ml to 5 mg/ml.

3. The method for treating urinary system disorders as recited in claim 1, wherein said carbon material further includes a metal particle combined with the carbon material, and the metal particle is one selected from the collection of silver, platinum, palladium, gold, zinc, copper and a combination of the above, and said metal particle has a diameter falling within a range from 10 nm to 2 mm, and occupies a percentage by weight of the carbon material below 20 wt %.

4. The method for treating urinary system disorders as recited in claim 3, wherein said metal particle further occupies a percentage by weight of the carbon material below 5 wt %.

5. The method for treating urinary system disorders as recited in claim 1, wherein said carbon material is one selected from the collection of carbon fiber, active carbon fiber, active carbon, nano-carbon tube, carbon nanocapsule, coke ball, carbon black, and a combination of the above.

6. The method for treating urinary system disorders as recited in claim 1, wherein said carbon material has a diameter falling within a range from 10 nm to 2 mm, and the carbon material has a carbon layer stack thickness (Lc) falling within a range from 1 nm to 1000 mm.

7. The method for treating urinary system disorders as recited in claim 1, wherein said water-containing carrier is a buffer solution or a combination of a buffer solution and an antibiotic medicament.

8. The method for treating urinary system disorders as recited in claim 7, wherein said antibiotic medicament is selected from the group consisting of Trimethoprim-sulfamethoxazole (TMP-SMX), Trimethoprim (TMP), sulfamethoxazole (SMX), fluoroquinolones, ciprofloxacin, ofloxacin, cephalexin, tetracycline, and a combination of the above.

9. The method for treating urinary system disorders as recited in claim 7, wherein said cystitis medication is selected from the group consisting of dimethyl sulfoxide, clorpactin, heparin, hyaluronic acid (HA), adriamycin (ADM), chondroitin sulfate, sodium bicarbonate, silver nitrite, pentosan polysulfate sodium, cromolyn sodium, pencillin, nitrofurazone, gentamicin, mild silver protein and a combination of the above.

10. The method for treating urinary system disorders as recited in claim 1, wherein said carbon material has a structure and specific surface area (BET) falling within a range from 700 $m^2/g$ to 1500 $m^2/g$.

11. The method for treating urinary system disorders as recited in claim 1, wherein said carbon material adsorbs endotoxins or lipopolysaccharide (LPS) of a bacteria.

12. The method for treating urinary system disorders as recited in claim 1, wherein said aqueous vehicle is selected from the group consisting of normal saline, phosphate buffered saline, and a combination thereof.

13. The method for treating urinary system disorders as recited in claim 1, wherein said urinary system disorders is selected from the collection group consisting of urinary tract infections (UTI), Catheter-Associated Urinary Tract Infection (CAUTI), bacterial induced cystitis, and a combination thereof.

14. The method for treating urinary system disorders as recited in claim 1, wherein said step of instilling is performed at least once weekly for a period of at least 6 weeks.

15. The method for treating urinary system disorders as recited in claim 1, wherein said step of instilling is performed at least twice weekly for a period of 1 week.

* * * * *